(12) United States Patent
Fung

(10) Patent No.: US 9,766,696 B1
(45) Date of Patent: Sep. 19, 2017

(54) APPARATUS FOR NATURAL TORSO TRACKING AND FEEDBACK FOR ELECTRONIC INTERACTION

(71) Applicant: Blue Goji LLC, Austin, TX (US)

(72) Inventor: Coleman Fung, Spicewood, TX (US)

(73) Assignee: Blue Goji LLC, Austin, TX (US)

( * ) Notice: Subject to any disclaimer, the term of this patent is extended or adjusted under 35 U.S.C. 154(b) by 0 days.

(21) Appl. No.: 15/175,043

(22) Filed: Jun. 7, 2016

Related U.S. Application Data

(60) Provisional application No. 62/310,568, filed on Mar. 18, 2016.

(51) Int. Cl.
*G06F 3/00* (2006.01)
*G06F 3/01* (2006.01)
*A61B 5/11* (2006.01)
*A61B 5/00* (2006.01)

(52) U.S. Cl.
CPC ............ *G06F 3/011* (2013.01); *A61B 5/1114* (2013.01); *A61B 5/6823* (2013.01); *G06F 3/016* (2013.01); *A61B 2503/12* (2013.01)

(58) Field of Classification Search
None
See application file for complete search history.

(56) References Cited

U.S. PATENT DOCUMENTS

| 4,410,852 A * | 10/1983 | Guretzky | G01R 27/2605 318/662 |
| 6,131,075 A * | 10/2000 | Tai | A63B 24/00 434/11 |
| 6,270,414 B2 * | 8/2001 | Roelofs | 345/156 |
| 8,025,607 B2 | 9/2011 | Ranky et al. | |
| 9,414,784 B1 | 8/2016 | Berme et al. | |
| 2009/0256800 A1 | 10/2009 | Kaufman | |

OTHER PUBLICATIONS

Roger E. Kaufman; A Family of New Ergonomic Harness Mechanisms for Full-Body Natural Constrained Motions in Virtual Environments; Mar. 10-11, 2007; IEEE; pp. 63-70.*
Roger E. Kaufman; Harness Mechanisms for Full-Body Motions in Virtual Environments; Mar. 10-14, 2007; IEEE; pp. 279-280.*

* cited by examiner

*Primary Examiner* — Idriss N Alrobaye
*Assistant Examiner* — Richard B Franklin
(74) *Attorney, Agent, or Firm* — Galvin Patent Law LLC; Brian R. Galvin

(57) ABSTRACT

An apparatus for natural torso tracking and feedback for electronic interaction, comprising a plurality of tethers each comprising a line with one end affixed to an attachment point at a fixed location distal from the body of a human user and with the other end being affixed to an attachment point proximal to the body of a human user, the proximal attachment point being configured to be worn or otherwise attached to a user's person or clothing, and at least a portion of the distal attachment points comprising a sensor configured to measure strain of an affixed tether.

9 Claims, 7 Drawing Sheets

APPARATUS FOR NATURAL TORSO TRACKING AND FEEDBACK FOR ELECTRONIC INTERACTION

CROSS-REFERENCE TO RELATED APPLICATIONS

The present application claims the benefit of and priority to U.S. provisional application Ser. No. 62/310,568 titled "APPARATUS FOR NATURAL TORSO TRACKING AND FEEDBACK FOR ELECTRONIC INTERACTION" filed on Mar. 18, 2016, the entire specification of which is incorporated herein by reference in its entirety.

BACKGROUND OF THE INVENTION

Field of the Art

The disclosure relates to the field of computer interaction, and more particularly to the field of input and output methods for interaction within software applications.

Discussion of the State of the Art

Computer and electronic device input methods have traditionally centered around the use of keyboards and pointer devices for many years. However, with the rapidly-expanding virtual reality industry, new interaction methods are being explored including a variety of controllers for gaming, wands, and motion-based input devices including gloves and camera-based hand tracking. However, these devices all focus on interacting with a user's hands, and ignore other parts of the body that could be used to improve interaction and immersion, while also expanding the possibilities for data collection.

What is needed, is a means to track the position, orientation, and movement of a user's whole body, to enable the use of their torso as a new input method. What is further needed, is a means to utilize a user's torso for two-way interaction, applying feedback to the user's body to facilitate a "whole body immersion" that is not possible through traditional control arrangements.

SUMMARY OF THE INVENTION

Accordingly, the inventor has conceived and reduced to practice, in a preferred embodiment of the invention, an apparatus for natural torso tracking and feedback for electronic interaction.

According to a preferred embodiment of the invention, an apparatus for natural torso tracking and feedback for electronic interaction, comprising a plurality of tethers each comprising a line with one end being affixed to an attachment point at a fixed location distal from the body of a human user and with the other end being affixed to an attachment point proximal to the body of a human user, the proximal attachment point being configured to be worn or otherwise attached to a user's person or clothing, and at least a portion of the distal attachment points comprising a sensor configured to measure at least strain of an affixed tether, is disclosed.

BRIEF DESCRIPTION OF THE DRAWING FIGURES

The accompanying drawings illustrate several embodiments of the invention and, together with the description, serve to explain the principles of the invention according to the embodiments. It will be appreciated by one skilled in the art that the particular embodiments illustrated in the drawings are merely exemplary, and are not to be considered as limiting of the scope of the invention or the claims herein in any way.

DETAILED DESCRIPTION

Figure 1:
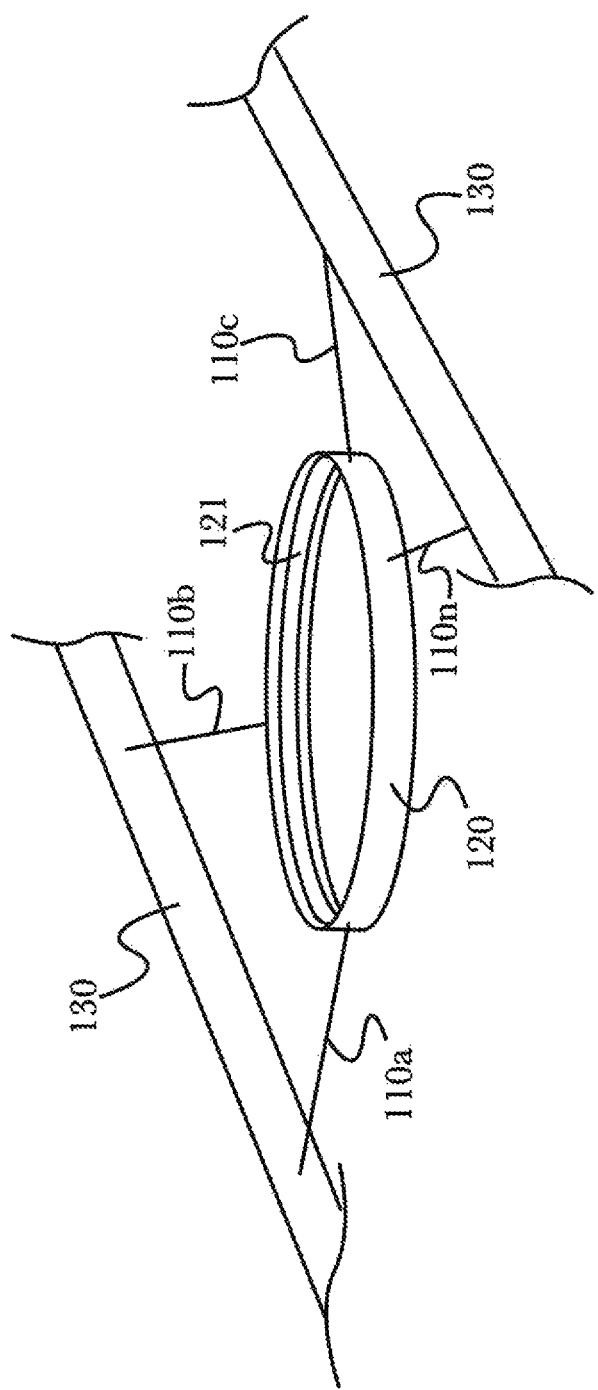
FIG. 1 is a diagram of an exemplary hardware arrangement of an apparatus for natural torso tracking and feedback for electronic interaction according to a preferred embodiment of the invention, illustrating the use of multiple tethers and a movable torso harness.

The inventor has conceived, and reduced to practice, in a preferred embodiment of the invention, an apparatus for natural torso tracking and feedback for electronic interaction.

One or more different inventions may be described in the present application. Further, for one or more of the inventions described herein, numerous alternative embodiments may be described; it should be appreciated that these are presented for illustrative purposes only and are not limiting of the inventions contained herein or the claims presented herein in any way. One or more of the inventions may be widely applicable to numerous embodiments, as may be readily apparent from the disclosure. In general, embodiments are described in sufficient detail to enable those skilled in the art to practice one or more of the inventions, and it should be appreciated that other embodiments may be utilized and that structural, logical, software, electrical and other changes may be made without departing from the scope of the particular inventions. Accordingly, one skilled in the art will recognize that one or more of the inventions may be practiced with various modifications and alterations. Particular features of one or more of the inventions described herein may be described with reference to one or more particular embodiments or figures that form a part of the present disclosure, and in which are shown, by way of illustration, specific embodiments of one or more of the inventions. It should be appreciated, however, that such features are not limited to usage in the one or more particular embodiments or figures with reference to which they are described. The present disclosure is neither a literal description of all embodiments of one or more of the inventions nor a listing of features of one or more of the inventions that must be present in all embodiments.

Headings of sections provided in this patent application and the title of this patent application are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an embodiment with several components in communication with each other does not imply that all such components are required. To the contrary, a variety of optional components may be described to illustrate a wide variety of possible embodiments of one or more of the inventions and in order to more fully illustrate one or more aspects of the inventions. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the invention(s), and does not imply that the illustrated process is preferred. Also, steps are generally described once per embodiment, but this does not mean they must occur once, or that they may only occur once each time a process, method, or algorithm is carried out or executed. Some steps may be omitted in some embodiments or some occurrences, or some steps may be executed more than once in a given embodiment or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other embodiments of one or more of the inventions need not include the device itself.

Techniques and mechanisms described or referenced herein will sometimes be described in singular form for clarity. However, it should be appreciated that particular embodiments may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of embodiments of the present invention in which, for example, functions may be executed out of order from that shown or discussed, including substantially concurrently or in reverse order, depending on the functionality involved, as would be understood by those having ordinary skill in the art.

Detailed Description of Exemplary Embodiments

FIG. 1 is a diagram of an exemplary hardware arrangement 100 for natural torso tracking and feedback for electronic interaction according to a preferred embodiment of the invention, illustrating the use of multiple tethers 110a-n and a movable torso harness 120. According to the embodiment, a plurality of tethers 110a-n may be affixed or integrally-formed as part of a handle or railing 130, such as handlebars found on exercise equipment such as a treadmill, elliptical trainer, stair-climbing machine, or the like. In alternate arrangements, specifically-designed equipment with integral tethers 110a-n may be used, but it may be appreciated that a modular design with tethers 110a-n that may be affixed and removed freely may be desirable for facilitating use with a variety of fitness equipment or structural elements of a building, according to a user's particular use case or circumstance. Tethers 110a-n may then be affixed or integrally-formed to a torso harness 120, as illustrated in the form of a belt, that may be worn by a user such that movement of their body affects tethers 110a-n and applies stress to them in a variety of manners. It should be appreciated that while a belt design for a torso harness 120 is shown for clarity, a variety of physical arrangements may be used such as including (but not limited to) a vest, a series of harness-like straps similar to climbing or rappelling equipment, a backpack, straps designed to be worn on a user's body underneath or in place of clothing (for example, for use in medical settings for collecting precise data) or a plurality of specially-formed clips or attachment points that may be readily affixed to a user's clothing. Additionally, a torso harness 120 may be constructed with movable parts, for example having an inner belt 121 that permits a user some degree of motion within the harness 120 without restricting their movement. Movement of inner belt 121 (or other movable portions) may be measured in a variety of ways, such as using accelerometers, gyroscopes, or optical sensors, and this data may be used as interaction with software applications in addition to data collected from tethers 110a-n as described below.

As a user moves, their body naturally shifts position and orientation. These shifts may be detected and measured via tethers 110a-n, for example by detecting patterns of tension or strain on tethers 110a-n to indicate body orientation, or by measuring small changes in strain on tethers 110a-n to determine more precise movements such as body posture while a user is speaking, or specific characteristics of a user's stride or gait. Additionally, through varying the quantity and arrangement of tethers 110a-n, more precise or specialized forms of movement may be detected and measured (such as, for example, using a specific arrangement of multiple tethers connected to a particular area of a user's body to detect extremely small movements for medical diagnosis or fitness coaching). This data may be used as interaction with software applications, such as for virtual reality applications as input for a user to control a character in a game. In such an arrangement, when a user moves, this movement may be translated to an in-game character or avatar to convey a more natural sense of interaction and presence. For example, in a multiplayer roleplaying game, this may be used to facilitate nonverbal communication and recognition between players, as their distinct mannerisms and gestures may be conveyed in the game through detection of natural torso position and movement. In fitness or health applications, this data may be used to track and monitor a user's posture or ergonomic qualities, or to assist in coaching them for specific fitness activities such as holding a pose for yoga, stretching, or proper running form during use with a treadmill. In medical applications, this data may be used to assist in diagnosing injuries or deficiencies that may require attention, such as by detecting anomalies in movement or physiological adaptations to an unrecognized injury (such as when a user subconsciously shifts their weight off an injured foot or knee, without consciously realizing an issue is present).

Through various arrangements of tethers 110a-n and tether sensors (as described below, referring to FIGS. 2-3), it may be possible to enable a variety of immersive ways for a user to interact with software applications, as well as to receive haptic feedback from applications. For example, by detecting rotation, tension, stress, or angle of tethers a user may interact with applications such as virtual reality games or simulations, by using natural body movements and positioning such as leaning, jumping, crouching, kneeling, turning, or shifting their weight in various directions to trigger actions within a software application configured to accept torso tracking input. By applying haptic feedback of varying form and intensity (as is described in greater detail below, referring to FIG. 2), applications may provide physical indication to a user of software events, such as applying tension to resist movement, pulling or tugging on a tether to move or "jerk" a user in a direction, or varying feedback to multiple tethers such as tugging and releasing in varying order or sequence to simulate more complex effects such as (for example, in a gaming use case) explosions, riding in a vehicle, or walking through foliage.

It should be appreciated that while reference is made to virtual reality applications, a wide variety of use cases may be possible according to the embodiment. For example, torso tracking may be used for fitness and health applications, to monitor a user's posture or gait while walking, without the use of additional virtual reality equipment or software.

Figure 2:
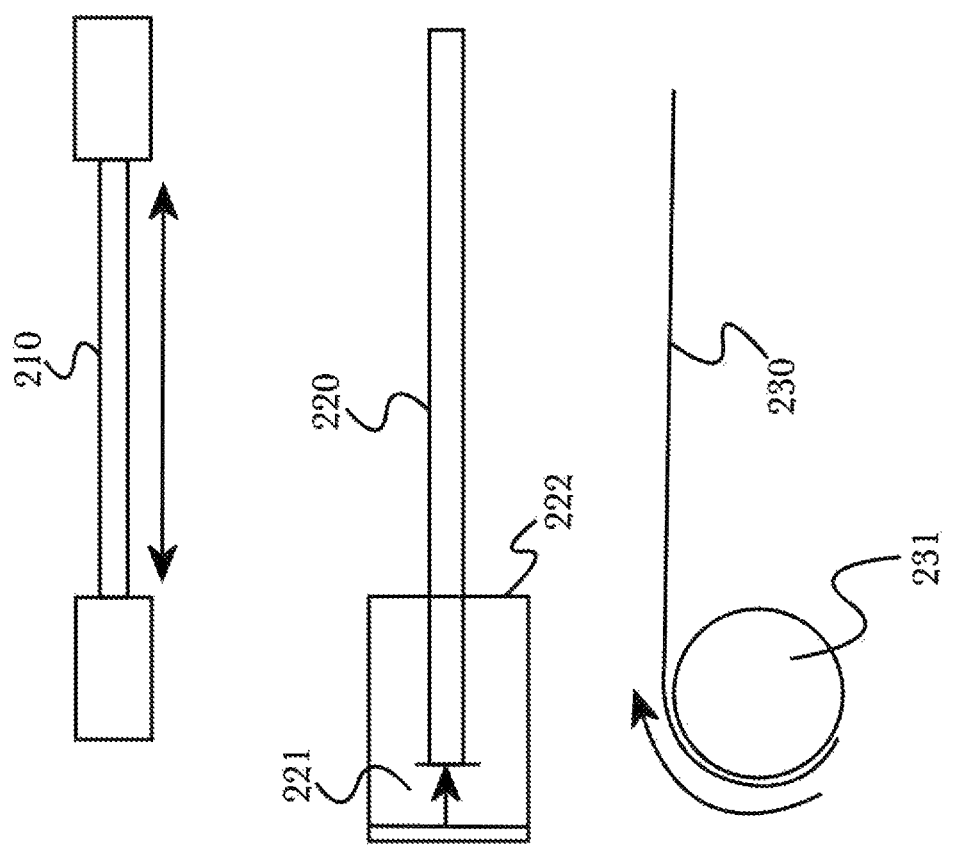
FIG. 2 is a diagram illustrating a variety of alternate tether arrangements.

FIG. 2 is a diagram illustrating a variety of alternate tether arrangements. According to various use cases and hardware arrangements, tethers 110a-n may utilize a variety of purpose-driven designs as illustrated. For example, a "stretchable" tether 210 may be used to measure strain during a user's movement, as the tether 210 is stretched or compressed (for example, using piezoelectric materials and measuring electrical changes). Such an arrangement may be suitable for precise measurements, but may lack the mechanical strength or durability for gross movement detection or prolonged use. An alternate construction may utilize a non-deforming tether 220 such as a steel cable or similar non-stretching material. Instead of measuring strain on the tether 220, instead tether 220 may be permitted a degree of movement within an enclosure 222 (for example, an attachment point on a torso harness 120 or handlebar 130), and the position or movement 221 of the tether 220 may be measured such as via optical sensors. In a third exemplary arrangement, a tether 230 may be wound about an axle or pulley 231, and may be let out when force is applied during a user's movement. Rotation of the pulley 231 may be measured, or alternately a tension device such as a coil spring may be utilized (not shown) and the tension or strain on that device may be measured as tether 230 is extended or retracted. In this manner, it may be appreciated that a variety of mechanical means may be used to facilitate tethers and attachments for use in detecting and measuring natural torso position and movement, and it should be appreciated that a variety of additional or alternate hardware arrangements may be utilized according to the embodiments disclosed herein.

Additionally, through the use of various hardware construction it becomes possible to utilize both "passive" tethers that merely measure movement or strain, as well as "active" tethers that may apply resistance or movement to provide haptic feedback to a user. For example, in an arrangement utilizing a coiled spring or pulley 231, the spring or pulley 231 may be wound to retract a tether and direct or impede a user's movement as desired. In this manner, various new forms of feedback-based interaction become possible, and in virtual reality use cases user engagement and immersion are increased through more natural physical feedback during their interaction.

By applying various forms and intensities of feedback using various tether arrangements, a variety of feedback types may be used to provide haptic output to a user in response to software events. For example, tension on a tether may be used to simulate restrained movement such as wading through water or dense foliage, walking up an inclined surface, magnetic or gravitational forces, or other forms of physical resistance or impedance that may be simulated through directional or non-directional tension. Tugging, retracting, or pulling on a tether may be used to simulate sudden forces such as recoil from gunfire, explosions, being grabbed or struck by a software entity such as an object or character, deploying a parachute, bungee jumping, sliding or falling, or other momentary forces or events that may be conveyed with a tugging or pulling sensation. By utilizing various patterns of haptic feedback, more complex events may be communicated to a user, such as riding on horseback or in a vehicle, standing on the deck of a ship at sea, turbulence in an aircraft, weather, or other virtual events that may be represented using haptic feedback. In this manner, virtual environments and events may be made more immersive and tangible for a user, both by enabling a user to interact using natural body movements and positioning, as well as by providing haptic feedback in a manner that feels natural and expected to the user. For example, if a user is controlling a character in a gaming application through a first-person viewpoint, it would seem natural that when their character is struck there would be a physical sensation corresponding to the event; however, this is not possible with traditional interaction devices, detracting from any sense of immersion or realism for the user. By providing this physical sensation alongside the virtual event, the experience becomes more engaging and users are encouraged to interact more naturally as their actions results in natural and believable feedback, meeting their subconscious expectations and avoiding excessive "immersion-breaking" moments, which in turn reduces the likelihood of users adopting unusual behaviors or unhealthy posture as a result of adapting to limited interaction schema.

Haptic feedback may be provided to notify a user of non-gaming events, such as for desktop notifications for email or application updates, or to provide feedback on their posture for use in fitness or health coaching. For example, a user may be encouraged to maintain a particular stance, pose, or posture while working or for a set length of time (for example, for a yoga exercise application), and if their posture deviates from an acceptable range, feedback is provided to remind them to adjust their posture. This may be used in sports, fitness, health, or ergonomic applications that need not utilize other aspects of virtual reality and may operate as traditional software applications on nonspecialized computing hardware. For example, a user at their desk may use an ergonomic training application that monitors their body posture throughout the work day and provides haptic reminders to correct poor posture as it is detected, helping the user to maintain a healthy working posture to reduce fatigue or injuries due to poor posture (for example, repetitive-stress injuries that may be linked to poor posture while working at a computer).

Figure 3:
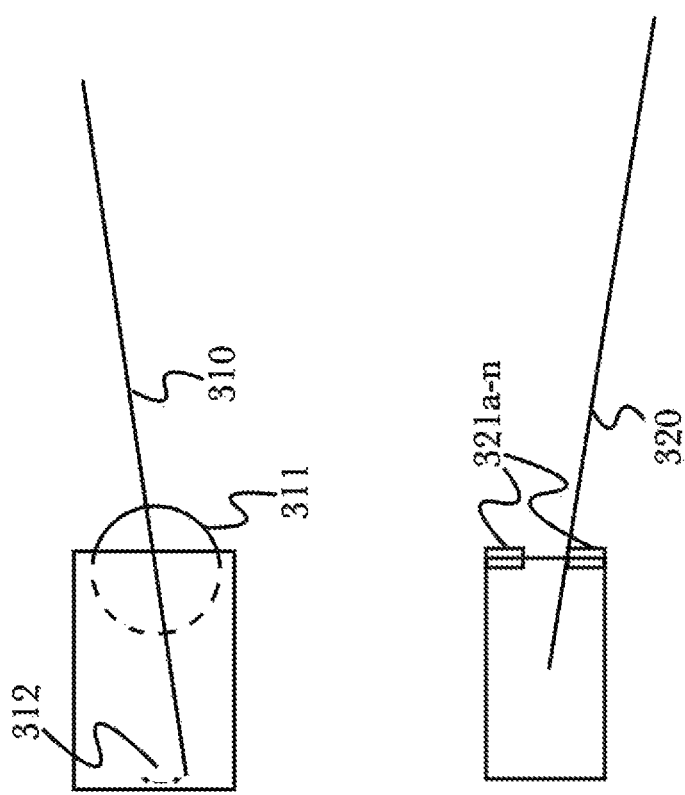
FIG. 3 is a diagram of an additional exemplary hardware arrangement of an apparatus for natural torso tracking and feedback for electronic interaction according to a preferred embodiment of the invention, illustrating the use of angle sensors to detect angled movement of tethers.

FIG. 3 is a diagram of an additional exemplary hardware arrangement 300 for natural torso tracking and feedback for electronic interaction according to a preferred embodiment of the invention, illustrating the use of angle sensors 312, 321a-n to detect angled movement of a tether 320. According to one exemplary arrangement, a tether 310 may be affixed to or passed through a rotating joint such as a ball bearing 311 or similar, to permit free angular movement. During movement, the angular movement or deflection 312 of a protruding bar, rod, or tether segment 313 may be measured (for example, using optical, magnetic, or other sensors) to determine the corresponding angle of tether 310. In this manner, precise angle measurements may be collected without impeding range of motion or introducing unnecessary mechanical complexity.

In an alternate hardware arrangement, the use of angle sensors 321a-n enables tracking of a vertical angle of a tether 320, to detect and optionally measure vertical movement or orientation of a user's torso. When tether 320 contacts a sensor 321a-n, this may be registered and used to detect a general vertical movement (that is, whether the tether is angled up or down). For more precise measurements, the specific hardware construction of a sensor 321a-n may be varied, for example using a pressure-sensing switch to detect how much force is applied and use this measurement to determine the corresponding angle (as may be possible given a tether 320 of known construction). It should be appreciated that various combinations of hardware may be used to provide a desired method or degree of angle detection or measurement, for example using a conductive tether 320 and a capacitive sensor 321a-n to detect contact, or using a mechanical or rubber-dome switch (as are commonly used in keyboard construction) to detect physical contact without a conductive tether 320.

The use of angle detection or measurement may expand interaction possibilities to encompass more detailed and natural movements of a user's body. For example, if a user crouches, then all tethers 110a-n may detect a downward angle simultaneously. Additionally, data precision or availability may be enhanced by combining input from multiple available sensors when possible (for example, utilizing adaptive software to collect data from any sensors that it detects, without requiring specific sensor types for operation), for example by combining data from tethers 110a-n and hardware sensors such as an accelerometer or gyroscope, enabling multiple methods of achieving similar or varied types or precision levels of position or movement detection. Similarly, when a user jumps then all tethers may detect an upward angle simultaneously. However, if a user leans in one direction, it may be appreciated that not all tethers 110a-n will detect the same angle. For example, tethers 110a-n in the direction the user is leaning may detect a downward angle, while those on the opposite side would detect an upward angle (due to the orientation of the user's torso and thus a worn torso harness 120). In this manner, more precise torso interaction may be facilitated through improved detection and recognition of orientation and movement. Additionally, it may be appreciated that sensors 321a-n may be utilized for other angle measurements, such as to detect horizontal angle. For example, if a user is wearing a non-rotating torso harness 120, when they twist their body a similar stress may be applied to all attached tethers 110a-n. Without angle detection the precise nature of this movement will be vague, but with horizontal angle detection it becomes possible to recognize that all tethers 110a-n are being strained in a similar direction (for example, in a clockwise pattern when viewed from above, as a user might view tethers 110a-n during use), and therefore interpret the interaction as a twisting motion (rather than, for example, a user squatting or kneeling, which might apply a similar stress to the tethers 110a-n but would have different angle measurements).

Figure 4:
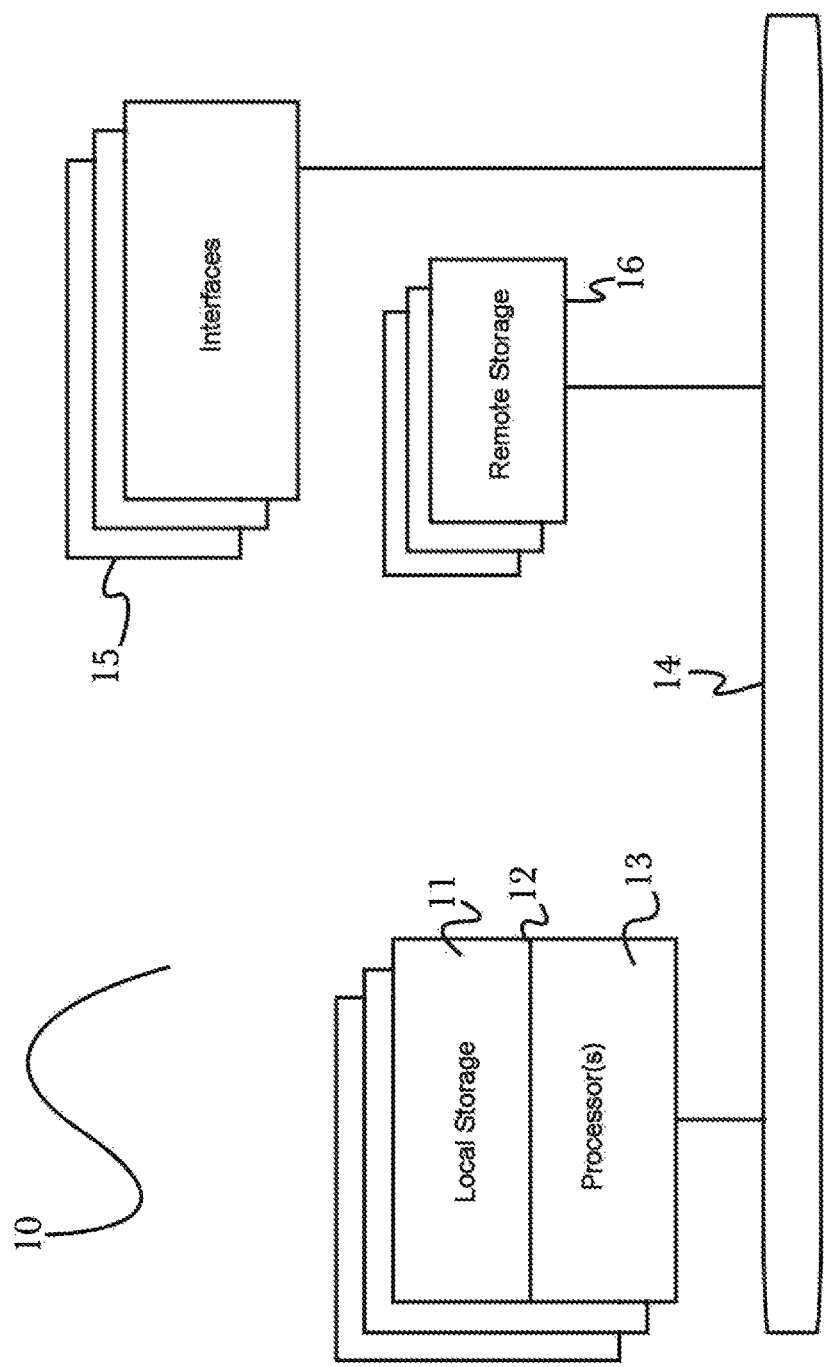
FIG. 4 is a block diagram illustrating an exemplary hardware architecture of a computing device used in an embodiment of the invention.

Referring now to FIG. 4, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one embodiment, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one embodiment, a computing device 10 may be configured or designed to function as a server system utilizing CPU 12, local memory 11 and/or remote memory 16, and interface(s) 15. In at least one embodiment, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some embodiments, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a specific embodiment, a local memory 11 (such as non-volatile random access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a Qualcomm SNAPDRAGON™ or Samsung EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one embodiment, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 4 illustrates one specific architecture for a computing device 10 for implementing one or more of the inventions described herein, it is by no means the only device architecture on which at least a portion of the features and techniques described herein may be implemented. For example, architectures having one or any number of processors 13 may be used, and such processors 13 may be present in a single device or distributed among any number of devices. In one embodiment, a single processor 13 handles communications as well as routing computations, while in other embodiments a separate dedicated communications processor may be provided. In various embodiments, different types of features or functionalities may be implemented in a system according to the invention that includes a client device (such as a tablet device or smartphone running client software) and server systems (such as a server system described in more detail below).

Regardless of network device configuration, the system of the present invention may employ one or more memories or memory modules (such as, for example, remote memory block 16 and local memory 11) configured to store data, program instructions for the general-purpose network operations, or other information relating to the functionality of the embodiments described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

Because such information and program instructions may be employed to implement one or more systems or methods described herein, at least some network device embodiments may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

Figure 5:
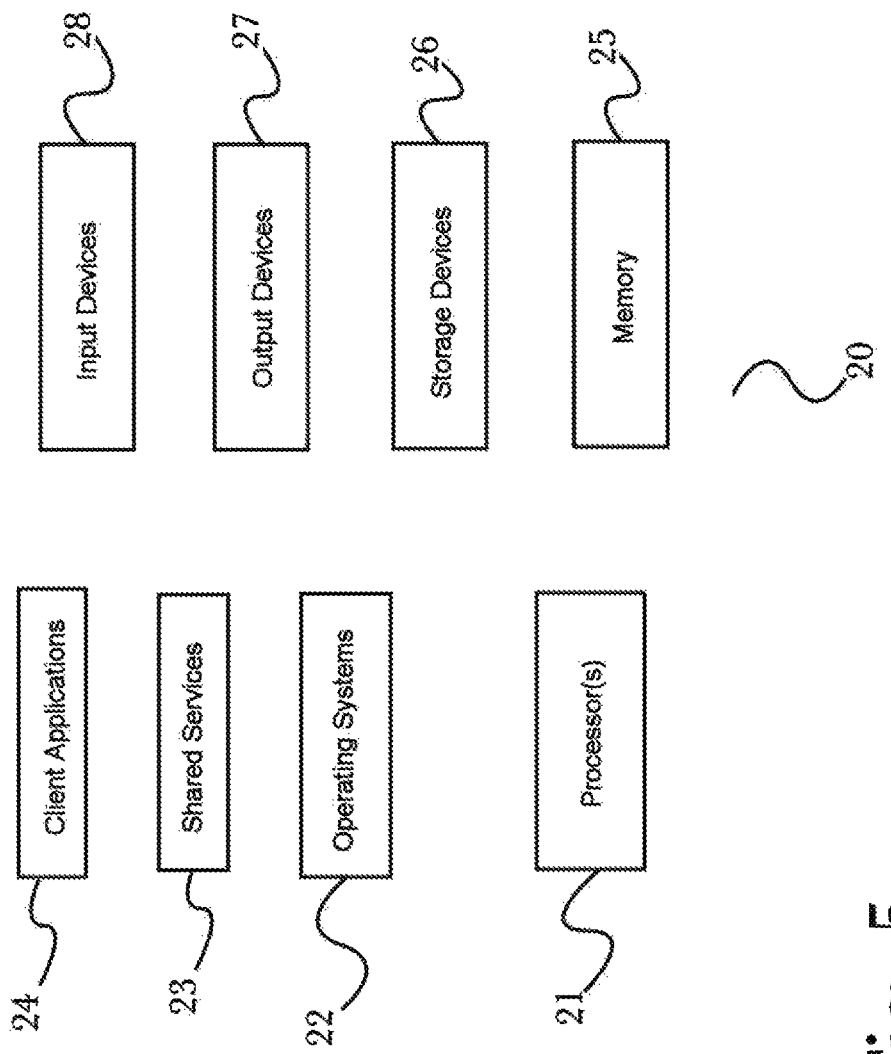
FIG. 5 is a block diagram illustrating an exemplary logical architecture for a client device, according to an embodiment of the invention.

In some embodiments, systems according to the present invention may be implemented on a standalone computing system. Referring now to FIG. 5, there is shown a block diagram depicting a typical exemplary architecture of one or more embodiments or components thereof on a standalone computing system. Computing device 20 includes processors 21 that may run software that carry out one or more functions or applications of embodiments of the invention, such as for example a client application 24. Processors 21 may carry out computing instructions under control of an operating system 22 such as, for example, a version of Microsoft's WINDOWS™ operating system, Apple's Mac OS/X or iOS operating systems, some variety of the Linux operating system, Google's ANDROID™ operating system, household gaming devices such as Microsoft XBOX™, Sony PLAYSTATION™, or virtual reality hardware devices such as Oculus RIFT™, HTC VIVE™, Samsung GEAR VR™, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 4). Examples of storage devices 26 include flash memory, magnetic hard drive, CD-ROM, and/or the like.

Figure 6:
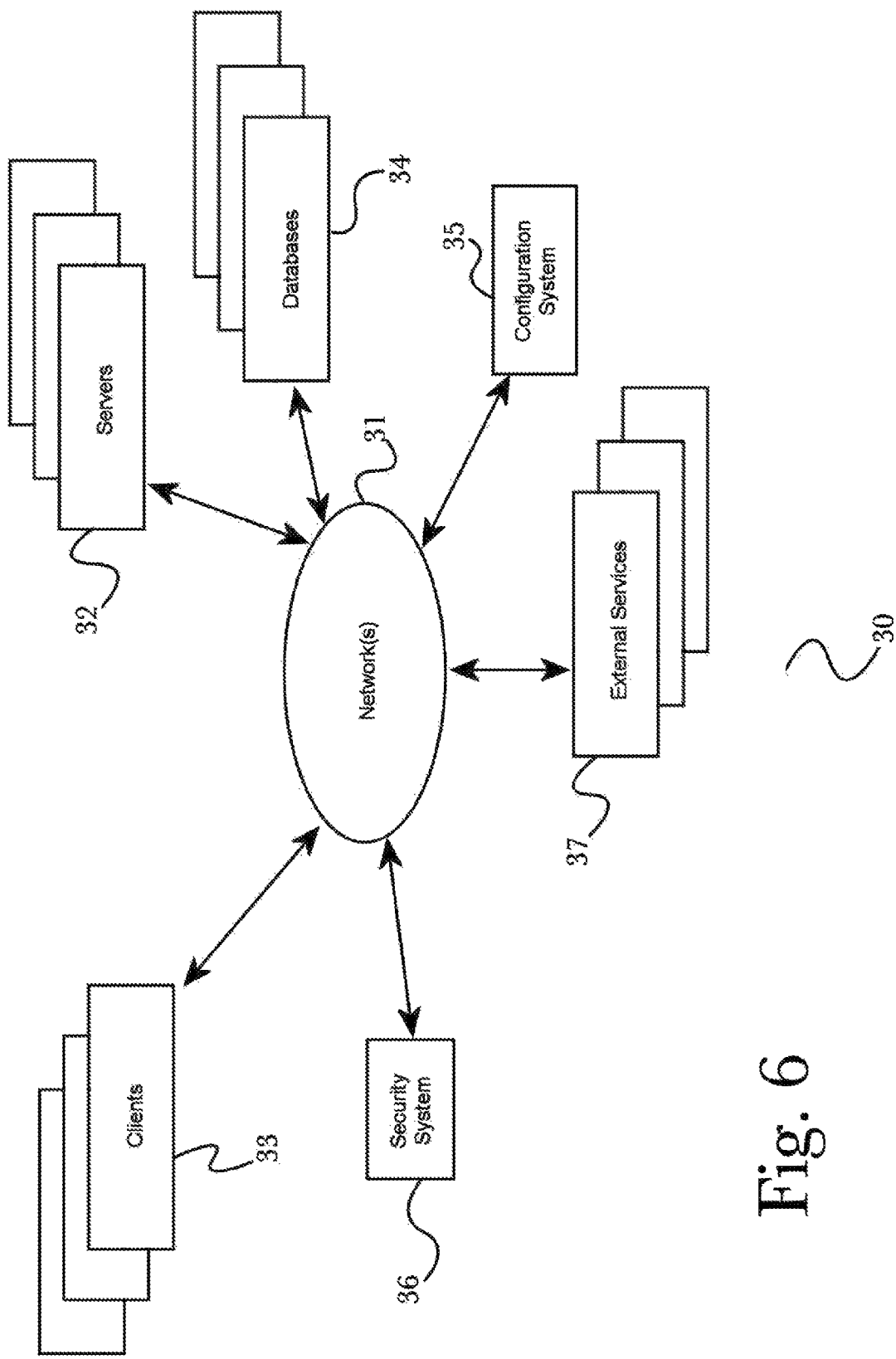
FIG. 6 is a block diagram showing an exemplary architectural arrangement of clients, servers, and external services, according to an embodiment of the invention.

In some embodiments, systems of the present invention may be implemented on a distributed computing network, such as one having any number of clients and/or servers. Referring now to FIG. 6, there is shown a block diagram depicting an exemplary architecture 30 for implementing at least a portion of a system according to an embodiment of the invention on a distributed computing network. According to the embodiment, any number of clients 33 may be provided. Each client 33 may run software for implementing client-side portions of the present invention; clients may comprise a system 20 such as that illustrated in FIG. 5. In addition, any number of servers 32 may be provided for handling requests received from one or more clients 33. Clients 33 and servers 32 may communicate with one another via one or more electronic networks 31, which may be in various embodiments any of the Internet, a wide area network, a mobile telephony network (such as CDMA or GSM cellular networks), a wireless network (such as WiFi, Wimax, LTE, and so forth), or a local area network (or indeed any network topology known in the art; the invention does not prefer any one network topology over any other). Networks 31 may be implemented using any known network protocols, including for example wired and/or wireless protocols.

In addition, in some embodiments, servers 32 may call external services 37 when needed to obtain additional information, or to refer to additional data concerning a particular call. Communications with external services 37 may take place, for example, via one or more networks 31. In various embodiments, external services 37 may comprise web-enabled services or functionality related to or installed on the hardware device itself. For example, in an embodiment where client applications 24 are implemented on a smartphone or other electronic device, client applications 24 may obtain information stored in a server system 32 in the cloud or on an external service 37 deployed on one or more of a particular enterprise's or user's premises.

In some embodiments of the invention, clients 33 or servers 32 (or both) may make use of one or more specialized services or appliances that may be deployed locally or remotely across one or more networks 31. For example, one or more databases 34 may be used or referred to by one or more embodiments of the invention. It should be understood by one having ordinary skill in the art that databases 34 may be arranged in a wide variety of architectures and using a wide variety of data access and manipulation means. For example, in various embodiments one or more databases 34 may comprise a relational database system using a structured query language (SQL), while others may comprise an alternative data storage technology such as those referred to in the art as "NoSQL" (for example, Hadoop Cassandra, Google BigTable, and so forth). In some embodiments, variant database architectures such as column-oriented databases, in-memory databases, clustered databases, distributed databases, or even flat file data repositories may be used according to the invention. It will be appreciated by one having ordinary skill in the art that any combination of known or future database technologies may be used as appropriate, unless a specific database technology or a specific arrangement of components is specified for a particular embodiment herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, most embodiments of the invention may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with embodiments of the invention without limitation, unless a specific security 36 or configuration system 35 or approach is specifically required by the description of any specific embodiment.

Figure 7:
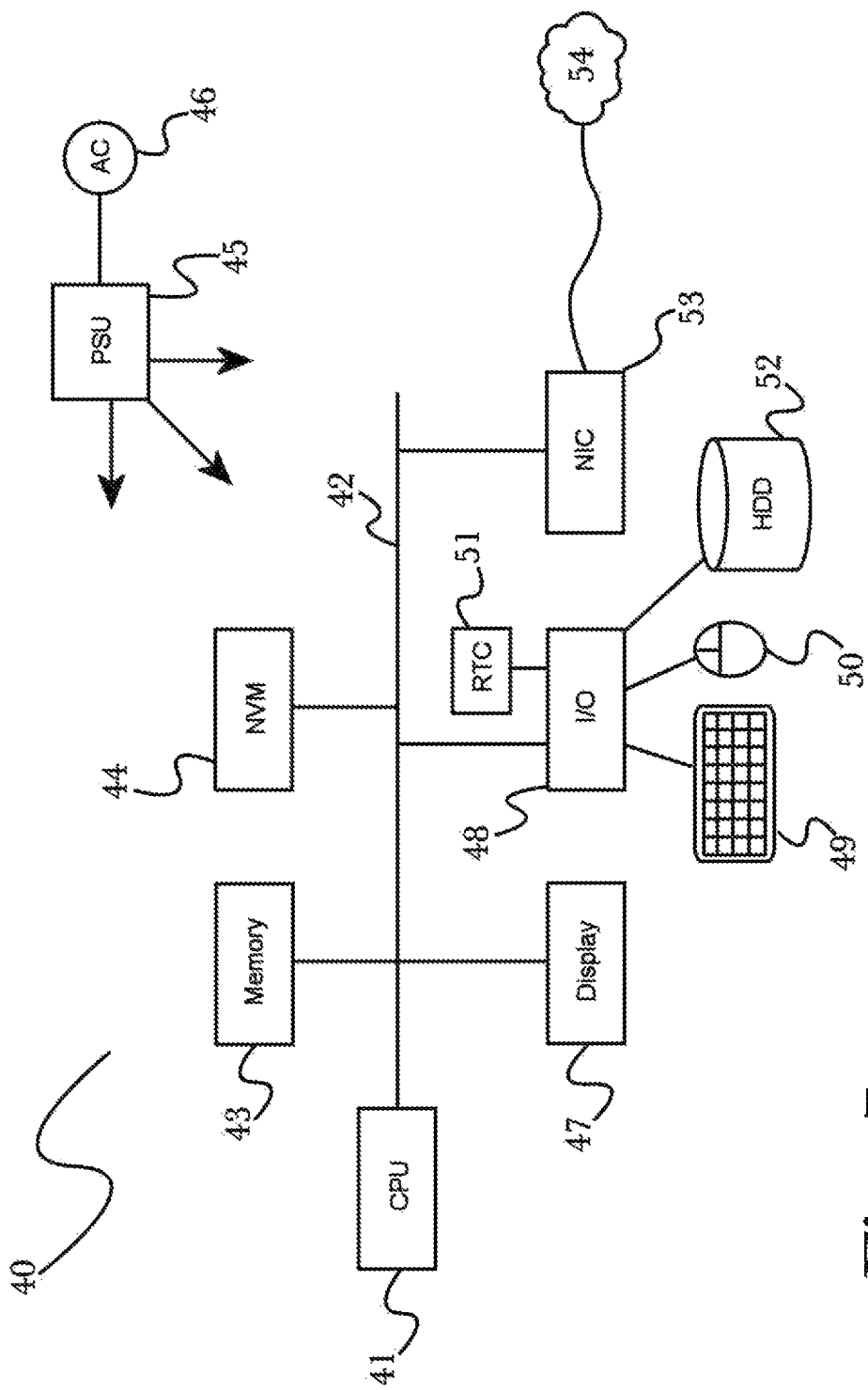
FIG. 7 is another block diagram illustrating an exemplary hardware architecture of a computing device used in various embodiments of the invention.

FIG. 7 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to keyboard 49, pointing device 50, hard disk 52, and real-time clock 51. NIC 53 connects to network 54, which may be the Internet or a local network, which local network may or may not have connections to the Internet. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various embodiments, functionality for implementing systems or methods of the present invention may be distributed among any number of client and/or server components. For example, various software modules may be implemented for performing various functions in connection with the present invention, and such modules may be variously implemented to run on server and/or client components.

The skilled person will be aware of a range of possible modifications of the various embodiments described above. Accordingly, the present invention is defined by the claims and their equivalents.

What is claimed is:

1. An apparatus for natural, three-dimensional torso tracking and feedback for electronic interaction, comprising:
    a plurality of tethers each comprising a line with one end being affixed to an attachment point at a fixed location distal from the body of a human user and with another end being affixed to an attachment point proximal to the body of the human user, the proximal attachment point being configured to be worn or otherwise attached to the human user's person or clothing, and at least a portion of the distal attachment points comprising a sensor configured to measure at least strain of the affixed tether; and a plurality of angle detection sensors, wherein at least a distal attachment point comprises an angle detection sensor configured to measure angular deflection of an affixed tether up or down with respect to a horizontal plane.

2. The apparatus of claim 1, further wherein at least an angle detection sensor further comprises an angle measurement device configured to measure the precise angle of an affixed tether.

3. The apparatus of claim 1, wherein an angle detection sensor comprises an electrical switch.

4. The apparatus of claim 3, wherein the electrical switch comprises a mechanical leaf switch.

5. The apparatus of claim 3, wherein the electrical switch comprises a rubber-dome switch.

6. The apparatus of claim 1, wherein an angle detection sensor comprises a capacitive sensor.

7. The apparatus of claim 1, wherein at least a distal attachment point comprises a mechanism for applying tension to an affixed tether.

8. The apparatus of claim 7, wherein the mechanism comprises at least a pulley.

9. The apparatus of claim 7, wherein the mechanism comprises at least a coiled spring.

* * * * *